United States Patent
Hart et al.

(10) Patent No.: US 7,109,203 B2
(45) Date of Patent: Sep. 19, 2006

(54) SULFONAMIDE DERIVATIVES

(75) Inventors: Terance W Hart, London (GB); Timothy J Ritchie, London (GB)

(73) Assignee: Novartis AG, Basel (CH)

( * ) Notice: Subject to any disclaimer, the term of this patent is extended or adjusted under 35 U.S.C. 154(b) by 496 days.

(21) Appl. No.: 10/475,420

(22) PCT Filed: May 13, 2002

(86) PCT No.: PCT/EP02/05240

§ 371 (c)(1),
(2), (4) Date: Oct. 22, 2003

(87) PCT Pub. No.: WO02/092556

PCT Pub. Date: Nov. 21, 2002

(65) Prior Publication Data

US 2004/0127533 A1  Jul. 1, 2004

Related U.S. Application Data

(60) Provisional application No. 60/290,827, filed on May 14, 2001.

(51) Int. Cl.
| | |
|---|---|
| C07C 311/19 | (2006.01) |
| C07D 213/55 | (2006.01) |
| C07D 239/26 | (2006.01) |
| C07D 257/04 | (2006.01) |
| A61K 31/18 | (2006.01) |
| A61P 29/00 | (2006.01) |

(52) U.S. Cl. ............ 514/256; 514/357; 514/381; 514/383; 514/562; 514/604; 544/335; 546/338; 548/252; 548/267.2; 548/255

(58) Field of Classification Search ............ 544/335; 546/338; 548/252, 267.2, 255; 560/12; 562/430; 564/90; 514/256, 357, 381, 383, 514/562, 604
See application file for complete search history.

(56) References Cited

U.S. PATENT DOCUMENTS

| | | | |
|---|---|---|---|
| 6,015,812 A | 1/2000 | Planchenault et al. ... | 514/235.8 |
| 6,958,331 B1 * | 10/2005 | Brain et al. .............. | 514/227.8 |

FOREIGN PATENT DOCUMENTS

| | | | |
|---|---|---|---|
| WO | WO 00 75107 A | | 12/2000 |
| WO | WO-2001024786 | * | 4/2001 |

OTHER PUBLICATIONS

Altamura et al., Regulatory Peptides, 80, 13-26, 1999.*
Bock et al., Current Opinion in Chemical Biology, 4, 401-406, 2000.*
Bhoola et al., Biol. Chem., 382, 77-89, 2001.*
Couture et al., European Journal of Pharmacology, 429, 161-176, 2001.*
Database STN International, File Medline, Accession No. 2005445418, Devani et al., Digestive and Liver Disease, 37(9), 665-673, Sep. 2005.*

* cited by examiner

*Primary Examiner*—Fiona T. Powers
(74) *Attorney, Agent, or Firm*—Peter J. Waibel; Joseph J. Borovian

(57) ABSTRACT

Sulfonamide derivitives of the formula I wherein $R^1$-$R^6$ are as defined in the description, processes for their production, their use as pharmaceuticals, particularly for use in the treatment or prevention of diseases in which bradykinin $B_1$ receptor activation plays a role or is implicated, and pharmaceutical compositions comprising them

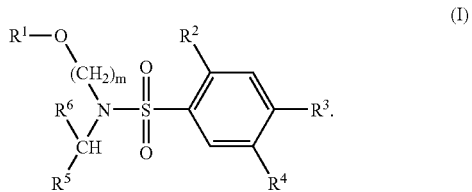

(I)

8 Claims, No Drawings

SULFONAMIDE DERIVATIVES

This application is a 371 of PCT/EP02/05240 filed May 13, 2002, which claims the benefit of U.S. provisional application No. 60/290,827, filed May 14, 2001, the contents of which are incorporated herein by reference.

The present invention relates to novel sulfonamide derivatives, to processes for their production, their use as pharmaceuticals and to pharmaceutical compositions comprising them.

More particularly the present invention provides in a first aspect, a compound of formula I

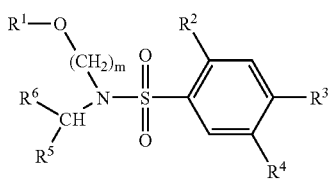

wherein
$R^1$ is phenyl, 1,2-dichlorophenyl, 3-methylphenyl, 3-bromophenyl, naphth-2-yl, indan-5-yl benzo[1,3]dioxol-5-yl or 1,2,3,4-tetrahydronaphth-6-yl;
$R^2$ is hydrogen, halogen, unsubstituted $C_1$–$C_4$alkyl or substituted $C_1$–$C_4$alkyl;
$R^3$ is hydrogen, halogen or $C_1$–$C_4$alkyl;
$R^4$ is hydrogen or $C_1$–$C_4$alkyl;
$R^5$ is hydrogen or $C_1$–$C_4$alkyl;
$R^6$ is $CH_2OH$; tetrazol-5-yl; 1,2,4-triazol-5-yl; 1,2,3-triazol-5-yl; C(O)OH, C(O)$NH_2$; or ZNH($CH_2$)$_n$CHR$^7$R$^8$, wherein Z is —C(O)— or —$CH_2$—, n is zero, 1, 2, 3 or 4;
$R^7$ is unsubstituted or substituted $C_1$–$C_4$alkyl, C(O)OH, C(O)O$C_1$–$C_4$alkyl;
$R^8$ is hydrogen, unsubstituted or substituted $C_1$–$C_4$alkyl, unsubstituted or substituted $C_5$–$C_{10}$aryl or heteroC$_5$–$C_{10}$aryl or $C_1$–$C_4$alkylC$_5$–$C_{10}$aryl or $C_1$–$C_4$alkyl-heteroC$_5$–$C_{10}$aryl, heteroC$_5$–$C_{10}$aryl comprising one or more heteroatoms selected from N, O, and S; and
m is 2, 3 or 4, in free form or in form of a salt.

On account of the asymmetrical carbon atom(s) present in the compounds of formula I and their salts, the compounds may exist in optically active form or in form of mixtures of optical isomers, e.g. in form of racemic mixtures. All optical isomers and their mixtures including the racemic mixtures are part of the present invention.

$C_1$–$C_4$alkyl, $C_5$–$C_{10}$aryl or heteroC$_5$–$C_{10}$aryl, when substituted may be one or more substituents selected from OH, C(O)OH, halogen, $C_1$–$C_4$alkyl, $C_1$–$C_6$alkoxy, benzyl, pyridinyl or pyrimidinyl. For example $C_1$–$C_4$alkyl may be substituted by OH, C(O)OH, $C_1$–$C_4$alkoxy, $C_1$–$C_4$alkyl, benzyl, pyridinyl or pyrimidinyl; phenyl may be substituted by one or more halogen, $C_1$–$C_4$alkyl or $C_1$–$C_6$alkoxy; benzyl may be substituted by one or more halogen or $C_1$–$C_6$alkoxy.

The compounds of the invention may exist in free form or in salt form, e.g. addition salts with e.g. organic or inorganic acids, for example trifluoroacetic acid or hydrochloride acid, or salts obtainable when they comprise a carboxy group, e.g. with a base, for example alkali salts such as sodium, potassium, or substituted or unsubstituted ammonium salts. Suitable pharmaceutically acceptable acid addition salts for pharmaceutical use in accordance with the invention include in particular the hydrochloride salt or sodium salt.

In formula I the following significances are preferred independently, collectively or in any combination or subcombination:
(a) $R^1$ is indan-5-yl;
(b) $R^2$ is hydrogen, Cl, Br, methyl or trifluoromethyl;
(c) $R^3$ is Cl or Br;
(d) $R^4$ is hydrogen or methyl;
(e) $R^5$ is hydrogen or methyl;
(f) $R^6$ is $CH_2OH$, C(O)$NH_2$, tetrazol-5-yl, C(O)OH or ZNH(CH$^2$)$_n$CHR$^8$R$^9$ wherein Z is —C(O)— or —$CH_2$—;
(g) n is zero or 1;
(h) $R^7$ is C(O)OH or $CH_2$C(O)OH;
(i) $R^8$ is phenyl; benzyl; 4,5-dimethoxyphenyl; 2-chlorobenzyl; 2-methoxybenzyl; 3-methoxybenzyl; 4-methoxybenzyl; $CH_2$-benzyl; $CH_2$-pyridin-3-yl or $CH_2$-pyrimidin-3-yl; and
(g) m is 2.

A preferred group are compounds wherein $R^1$ is indan-5-yl; $R^2$ is Cl; $R^3$ is Cl or Br; $R^4$ is hydrogen; $R^5$ is hydrogen; $R^6$ is C(O)OH or C(O)NH(CH$_2$)$_n$CHR$^7$R$^8$ wherein n is zero or 1, $R^7$ is C(O)OH or $CH_2$C(O)OH; and $R^8$ is phenyl, benzyl, 4,5-dimethoxyphenyl, 2-chlorobenzyl, 2-methoxybenzyl, 3-methoxybenzyl, 4-methoxybenzyl, $CH_2$-benzyl or $CH_2$-pyrimidin-3-yl; and m is 2.

In addition to the foregoing, the present invention also provides a process for the production of a compound of formula I and its salts, comprising
(a) for the production of a compound of formula I wherein $R^6$ is C(O)OH, deprotecting a compound of formula II

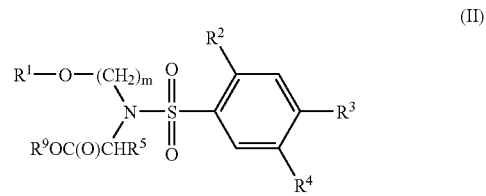

wherein $R^1$, $R^2$, $R^3$, $R^4$, $R^5$ and m are as defined above and $R^9$ is $C_1$–$C_4$alkyl; or (b) for the production of a compound of formula I wherein, $R^6$ is C(O)$NH_2$ or ZNH(CH$_2$)$_n$CHR$^7$R$^8$ wherein Z is —C(O)— and n, $R^7$ and $R^8$ are as defined above, reacting a compound of formula I wherein $R^6$ is C(O)OH with $NH_3$ or a compound of formula III

HNH(CH$_2$)$_n$CHR$^7$R$^8$     (III)

wherein n, $R^7$, and $R^8$ are as defined above, and optionally further derivatising the resulting compound; or (c) for the production of a compound of formula I wherein, $R^6$ is $CH_2OH$; tetrazol-5-yl; 1,2,4-triazol-5-yl and 1,2,3-triazol-5-yl or ZNH(CH$_2$)$_n$CHR$^7$R$^8$ wherein Z is —$CH_2$— and n, $R^7$ and $R^8$ are as defined above, reacting a compound of formula IV

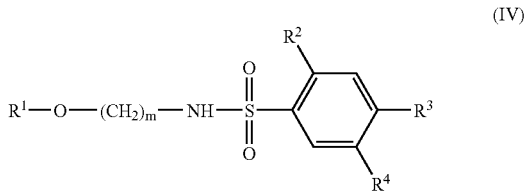

wherein $R^1$, $R^2$, $R^3$, $R^4$ and m are as defined above, with a compound of formula V

wherein $R^5$ is as defined above, $R^6$ is $CH_2OH$, tetrazol-5-yl; 1,2,4-triazol-5-yl and 1,2,3-triazol-5-yl or $ZNH(CH_2)_n$ $CHR^7R^8$ wherein Z is $-CH_2-$ and n, $R^7$ and $R^8$ are as defined above and Hal is halogen;

and recovering the so obtained compound of formula I in free form or in form of a salt.

Optionally, a compound of formula (III), (V) or (VI) may be used in protected form in processes (b), (c), or (d) and the resulting compound deprotected after the reaction.

Compounds of formula II are novel and also part of the present invention. They may be prepared, e.g. by reacting a compound of formula IV wherein $R^1$, $R^2$, $R^3$, $R^4$ and m are as defined above, with a compound of formula VI

wherein $R^5$ and $R^9$ are as defined above and Hal is halogen.

The reaction may be carried out in accordance with standard procedures, for example as illustrated for processes (a) and (b) in example 1. Alternatively, derivatives where $R^6$ is a heterocyclic group, such as tetrazol-5-yl, may be prepared from compounds of formula I where $R^6$ is C(O)OH, via appropriate amide intermediates, using known standard procedures, for example as illustrated in example 2. Work up of the reaction mixture can be effected by conventional procedures. The salt forms are made by standard procedures known to the skilled artisan.

Starting compounds of formula III, IV, V, and VI are known or may be prepared from corresponding known compounds.

The compounds of the invention and their pharmaceutically acceptable salts (hereinafter agents of invention) have pharmacological activity and are useful as pharmaceuticals. In particular, the agents of invention exhibit bradykinin antagonist activity. In particular, the agents of invention, e.g. the compound of examples 1–35 are active at the human $B_1$ bradykinin receptor.

Bradyidnin receptor interaction of the agents of invention is demonstrated by their ability to displace desArg[10]kallidin at human bradykinin $B_1$ receptor sites, e.g. as demonstrated in accordance with the following test method.

Test I: Bradykinin Receptor Binding Assay

WI-38 cells are grown in Dulbecco's Modified Eagle Medium s supplemented with 1% non-essential amino acids, 2 mM L-glutamine, 100 IU/ml penicillin, 100 μg/ml streptomycin and 10% foetal calf serum. The cells are grown in 175 cm$^2$ tissue culture flasks and split approximately 1–2 times a week at a ratio of 1:2 using trypsin to detach the cells. WI-38 cells are plated onto 24 well plates at approximately 50,000 cells per well and grown overnight. To upregulate expression of the $B_1$ receptor the cells are treated with 100 units/ml of IL-1β for 3 hours prior to the assay. The binding buffer is 10 mM HEPES in Hank's Balanced Salt solution pH 7.4 plus 1 mM phenanthroline and 0.14 mg/ml bacitracin. The cells are incubated for 1 h at 4° C. in binding buffer containing the radioligand [$^3$H]-desArg[10]kallidin in a volume of 500 μl. Non-specific binding is determined with 3 μM desArg[10]kallidin. At the end of the incubation the cells are washed 3 times with 50 mM Tris-HCl pH 7.4 containing 300 mM sucrose. The cells are solubilised with 0.2% SDS and the amount of radioactivity in the samples determined by liquid scintillation counting. The affinity constant ($K_d$) is obtained by incubating the cells with a range of [$^3$H]-desArg[10]kallidin concentrations. For displacement experiments the cells are incubated with approximately 1 nM [$^3$H]-desArg[10]kallidin and various concentrations of test compound. Compounds are made up in DMSO and diluted into binding buffer to give a final DMSO concentration of 0.5%.

Results are calculated by subtracting the value for non-specific binding from all values and calculating the amount of binding for each concentration of compound as a percentage of the specific binding with no compound. The $IC_{50}$ values are calculated in ORIGIN using a logistic fit. $K_I$ values are calculated from the $IC_{50}$ values using the Cheng-Prussoff equation ($K_I=IC_{50}/(1+([RL]/K_d))$) where [RL] is the radioligand concentration.

$K_I$ values are 0.063 μM for the peptide antagonist desArg[10]HOE140 [(D-Arg-[Hyp[3], Thi[5], D-Tic[7], Oic[8]]de-sArg[9] bradykinin)=(D-Arginine-[hydroxyproline[3], thienyamine[5], D-tetrahydroxyquinoline-3-carboxylic acid[7], octahydroindole-2-carboxylic acid[8]]desArginine[9] bradykinin)] and in the range of 0.5 nM to 2 μM for agents of invention.

Activity specifically as anti-hyperalgesic agents may be demonstrated in accordance with standard test methods, e.g. as described in the following test.

Test II: Thermal Antinociceptlon in Monkeys (Warm Water Tall-Wlthdrawal)

Carrageenan at a dosage of 2 mg in 100 μl saline is injected subcutaneously into the terminal 1 to 4 cm of the tail of adult rhesus monkeys (*Macaca mulatta*) followed by administration of Pharmaceutical Compound in 100 μl vehicle (50% PEG400-saline) or vehicle to the animal. The animals are seated in restraint chairs and the lower part of the shaved tail (approximately 15 cm) immersed into warm water maintained at temperatures of 42, 46, and 50° C. Tail-withdrawal latencies are recorded manually by a computerized timer. A maximum cutoff latency (20 sec) is recorded if the subjects fail to remove their tails by this time. A single dosing procedure is used in all test sessions. Each experimental session begins with control determinations at each temperature. Subsequent tail withdrawal latencies are determined based on each experimental condition. The subjects are tested 1 to 2 times at three temperatures in a varying order, with approximately 1 to 2 min interval between tests. Experimental sessions are conducted once per week.

In this test the agents of invention are efficient in preventing or reversing carrageenan-induced hyperalgesia at a dosage in the range of from 0.01 µMol/kg to 1 mMol/kg.

The agents of the invention are thus in particular useful as bradykinin $B_1$ receptor antagonists, e.g. for the treatment of pain of various genesis or aetiology and as anti-inflammatory and/or anti-oedemic agents for the treatment of inflammatory reactions, diseases or conditions, as well as for the treatment of allergic responses. Having regard to their analgesic/anti-inflammatory profile they are useful for the treatment of inflammatory pain, for the treatment of hyperalgesia and, in particular, for the treatment of severe chronic pain. They are, for example, useful for the treatment of pain, inflammation and/or oedema consequential to trauma, e.g. associated with burns, sprains, fracture or the like, subsequent to surgical intervention, e.g. as post-operative analgesics, as well as for the treatment of inflammatory pain of diverse genesis, e.g. for the treatment of bone and joint pain (osteoarthritis), rheumatoid arthritis, rheumatic disease, teno-synovitis, gout, cancer pain, myofascial pain (muscular injury, fibromyalgia), chronic neuropathic pain, e.g. diabetic neuropathy, phantom limb pain and perioperative pain (general surgery, gynecologic surgery). They are further suitable as analgesics for the treatment of pain associated with, e.g., angina, menstruation or cancer. As anti-inflammatory/anti-oedema agents, they are further useful, e.g., for the treatment of inflammatory skin disorders, for example psoriasis and eczema.

The agents of the invention may also be useful in other pathophysiological conditions where bradykinin $B_1$ receptors are upregulated, for example in tissues during acute transplant rejection and in renal glomerular disease. The agents of the invention may also be useful to reduce angiogenesis associated with tumor growth for example in oesophageal, renal and gastric carcinomas. The contents of a review describing the involvement of bradykinin $B_1$ receptors is incorporated herewith by reference (Bhoola et al 2001, Biol Chem; 382:77–89).

The agents of the invention are also useful as smooth muscle relaxants, e.g. for the treatment of spasm of the gastrointestinal tract or uterus, e.g. in the treatment of glaucoma/intra-ocular pressure, e.g. in the therapy of Crohn's disease, ulcerative colitis or pancreatitis and for the treatment of muscle spasticity and tremor in e.g. multiple sclerosis.

For the above indications the appropriate dosage of the agents of the invention will, of course, vary depending upon, for example, the host, the mode of administration and the nature and severity of the condition being treated as well as the relative potency of the particular agent of the invention employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 20.0 mg/kg p.o. In humans, an indicated daily dosage Is in the range of from about 0.7 to about 1400 mg/day p.o., e.g. from about 50 to 200 mg, conveniently administered once or in divided doses up to 4× per day or in sustained release form. Oral dosage forms accordingly suitably comprise from about 0.2 to about 700 mg of an agent of the invention admixed with an appropriate pharmaceutically acceptable diluent or carrier.

The agents of the invention may alternatively be administered e.g. topically in the form of a cream, gel or the like for example for the treatment of conditions of the skin as hereinbefore described or by inhalation, e.g. in dry powder form, for example for the treatment of asthma. Examples for compositions comprising an agent of the invention include, e.g. a solid dispersion, an aqueous solution, e.g. containing a solubilising agent, a microemulsion and a suspension of, e.g. a hydrochloride salt of a compound of formula I in the range of from 0.1 to 1%, e.g. 0.5%. The composition may be buffered to a pH in the range of, e.g. from 3.5 to 9.5, e.g. to pH 4.5, by a suitable buffer.

The agents of the invention are also useful as research chemicals.

The agents of the invention can be administered in vivo either alone or in combination with other pharmaceutical agents effective in the treatment of diseases and conditions in which bradykinin $B_1$ receptor activation plays a role or is implicated including cyclooxygenase-2 (COX-2) inhibitors, such as specific COX-2 inhibitors (e.g. celecoxib, COX189, and rofecoxib) or in general nonsteroidal anti-inflammatory drugs (NSAIDs) (e.g. acetylsalicylic acid, propionic acid derivatives), vanilloid receptor antagonists, tricyclic antidepressants (e.g. Anafranil®, Asendin®, Aventyl®, Elavil®, Endep®, Norfranil®, Norpramin®, Pamelor®, Sinequan®, Surmonfil®, Tipramine®, Tofranil®, Vivactil®, Tofranil-PM®, anticonvulsants (e.g. gabapentin), and $GABA_B$ agonists (e.g. L-baclofen).

The pharmaceutical compositions for separate administration of the combination partners and for the administration in a fixed combination, i.e. a single galenical composition comprising at least two combination partners, according to the invention can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Novel pharmaceutical compositions contain, for example, from about 0.1% to about 99.9%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partners may be administered simultaneously or sequentially and in any order, and the components may be administered separately or as a fixed combination. For example, the method of delay of progression or treatment of a proliferative disease according to the invention may comprise (i) administration of the combination partner (a) in free or pharmaceutically acceptable salt form and (ii) administration of a combination partner (b) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners can be administered separately at different times during the course of therapy or concurrently in divided or single combination forms. Furthermore, the term administering also encompasses the use of a pro-drug of a combination partner that converts in vivo to the combination partner as such. The instant invention is therefore to be understood as embracing all such regimes of simultaneous or alternating treatment and the term "administering" is to be interpreted accordingly.

The effective dosage of each of the combination partners employed may vary depending on the particular compound or pharmaceutical composition employed, the mode of administration, the condition being treated, the severity of the condition being treated. Thus, the dosage regimen is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active Ingredients' availability to target sites. In general, satisfactory results in animals are indicated to be obtained at daily dosages of from about 0.01 to about 20.0 mg/kg p.o. In humans, an indicated daily dosage is in the range of from about 0.7 to about 1400 mg/day p.o., e.g. from about 50 to 200 mg, conveniently administered once or in divided doses up to 4× per day or in sustained release form. Oral dosage forms accordingly suitably comprise from about 0.2 to about 700 mg.

In accordance with the foregoing, the present invention also provides:

(1) An agent of the invention for use as a pharmaceutical, for example for use as a bradykinin $B_1$ receptor antagonist in any of the particular indications hereinbefore set forth;

(2) A pharmaceutical composition comprising an agent of the invention as active ingredient together with a pharmaceutically acceptable diluent or carrier therefore, e.g. for the treatment or prevention of a disease or condition in which bradykinin $B_1$ receptor activation plays a role or is implicated;

(3) A method for treating or preventing a disease or condition in which bradykinin $B_1$ receptor activation plays a role or is implicated, comprising administering to a mammal in need thereof a therapeutically effective amount of an agent of the invention;

(4) The use of an agent of the invention as a pharmaceutical.

(5) The use of an agent of the invention for the manufacture of a medicament for the treatment or prevention of a disease or condition in which bradykinin $B_1$ receptor activation plays a role or is implicated;

(6) A combination comprising a therapeutically effective amount of an agent of the invention and a second drug substance, said second drug substance being for example for use in any of the particular indications hereinbefore set forth.

The following examples illustrate the invention.

EXAMPLE 1

Preparation of (S)-3-(2-{(4-bromo-2-chloro-benzenesulfonyl)-[2-(indan-5-yloxy)-ethyl]-amino}-acetylamino)-4-phenyl-butyric Acid A stirred solution of 4-bromo-2-chloroaniline (3.99 g) in acetic acid (90 ml) at 15° C. is treated with concentrated hydrochloric acid (22 ml), followed by a solution of sodium nitrite (1.29 g) in water (4.5 ml) at 10° C. After 30 min, the mixture is added to a stirred solution of sulfur dioxide (32 g) and copper II chloride (1.3 g) in acetic acid (128 ml) and water (6.4 ml), also at 10° C. After stirring for a further 16 hours, the mixture is diluted with ice-cold water (500 ml) and extracted with ethyl acetate (4×100 ml). The combined extracts are washed successively with water (4×100 ml) and then brine, dried over magnesium sulfate, filtered and evaporated to give crude 2-chloro-4-bromobenzenesulfonyl chloride.

A stirred suspension of 2-[(2,3-dihydro-1H-indan-5-yl)oxy]-ethanamine (2.4 g) and cesium carbonate (18.0 g) in dry DMF (52 ml) at room temperature is treated with 2-chloro-4-bromobenzenesulfonyl chloride (4.0 g). After 5 hours, the reaction mixture is treated with methyl bromoacetate (2.09 g) and the mixture stirred for a further 24 hours. The reaction mixture is diluted with ethyl acetate (200 ml) and washed successively with sodium bicarbonate solution (2×50 ml), water (2×50 ml), and brine (50 ml). After drying over magnesium sulfate and filtration, the ethyl acetate is evaporated to give a oil, which is purified by column chromatography on silica gel (eluent: ethyl acetate-cyclohexane 1:3) to give {(4-bromo-2-chloro-benzenesulfonyl)-[2-(indan-5-yloxy)-ethyl]-amino}-acotic acid methyl ester.

A stirred solution of {(4-bromo-2-chloro-benzenesulfonyl)-[2-(indan-5-yloxy)-ethyl]-amino}-acetic acid methyl ester (2.8 g) in THF (22 ml)-water (22 ml) at 15° C. is treated dropwise with 1 M aqueous sodium hydroxide solution (28 ml), and the resulting mixture stirred for 3 hours. The mixture is then diluted with ice-cold water (200 ml), acidified to pH 1 with 1 M hydrochloric acid, and extracted with ethyl acetate (2×100 ml). The combined extracts are washed successively with water (100 ml) and then brine, dried over magnesium sulfate, filtered and evaporated. The resulting solid is triturated with hexane, collected by filtration and dried, to afford {(4-bromo-2-chloro-benzenesulfonyl)-[2-(indan-5-yloxy)-ethyl]-amino}-acetic acid [retention time 7.6 min/HPLC conditions: Kingsorb 3 micron, 30×4.6 mm C 18 column, Gradient elution 10 to 100% acetonitrile in water (+0.1% trifluoroacetic acid) over 10 min]. $^1$H NMR (DMSO-$d_6$) δ=12.88 (broad s, 1H), 7.94 (d, 1H), 7.90 (d, 1H), 7.71 (dxd, 1H), 7.03 (d, 1H), 6.50 (s, 1H), 6.43 (dxd, 1H), 4.26 (s, 2H), 3.97 (t, 2H), 3.65 (t, 2H), 2.79 (t, 2H), 2.75 (t, 2H), 1.98 (m, 2H).

A stirred solution of {(4-bromo-2-chloro-benzenesulfonyl)-[2-(indan-5-yloxy)-ethyl]-amino}-acetic acid (112 mg) and t-butyl-(3S)-3-amino-4-phenylbutanoate (50 mg) in dry DMF (3 ml) at room temperature, is treated with N-methylmorpholine (60 μl), hydroxybenzotriazole (34 mg) and 1-ethyl-3-[3-(dimethylamino)propyl]carbodiimide (53 mg). After 24 hours, the mixture is diluted with ethyl acetate (100 ml) and washed successively with water (2×200 ml), sodium bicarbonate solution, and brine. After drying over magnesium sulfate and filtration, the ethyl acetate is evaporated to dryness. Column chromatography on silica gel affords pure (S)-3-(2-{(4-bromo-2-chloro-benzenesulfonyl)-[2-(indan-5- yloxy)-ethyl]-amino}-accetylamino)-4-phenyl-butyric acid tert-butyl ester (130 mg), which is then dissolved in a 1:4 mixture of trifluoroacetic acid-dichloromethane (4 ml). After stirring at room temperature for 16 hours, the solution is evaporated to dryness and triturated with diethyl ether to give a colourless precipitate, which is collected by filtration and dried to give Example (1) [retention time 8.0 min/HPLC conditions: Kingsorb 3 micron, 30×4.6 mm C 18 column, Gradient elution 10 to 100% acetonitrile in water (+0.1% trifluoroacetic acid) over 10 min, flow rate=3 ml/min; ion mass $MH^+$=629)]. 1H NMR (DMSO-$d_6$) δ=8.1 (d, 1H), 7.9 (m, 2H), 7.7 (d, 1H), 7.3 (m, 2H), 7.25 (m, 3H), 7.2 (d, 1H), 6.5 (s, 1H), 6.4 (d, 1H), 4.1 (m, 1H), 4.0 (q, 2H), 3.9 (t, 2H), 3.55 (m, 1H), 3.4 (m, 1H), 2.8 (m, 5H), 2.7 (m, 1H), 2.3 (m, 2H), 2.0 (m, 2H).

In the following examples compounds of formula I wherein $R^1$ is indan-5-yl, $R^5$ is hydrogen or methyl and m is 2 are prepared analogously to example 1.

| Example | $R^2$ | $R^3$ | $R^4$ | $R^5$ | $R^6$ |
|---|---|---|---|---|---|
| 2 | Cl | Cl | H | H | C(O)NH$_2$ |
| 3 | Cl | Cl | H | H | C(O)OH |
| 4 | Cl | Cl | CH$_3$ | H | C(O)OH |
| 5 | Cl | Br | H | H | C(O)OH |
| 6 | Cl | Cl | H | CH$_3$ | C(O)NH(CH$_2$)$_2$C(O)OH |

In the following examples compounds of formula I wherein $R^1$ is indan-5-yl, $R^4$ are hydrogen, $R^6$ is ZNH(CH$^2$)$_n$CHR$^7$R$^8$ and m is 2 are prepared according to example 1.

| Example | Z | $R^2$ | $R^3$ | $R^5$ | $R^7$ | $R^8$ | n |
|---|---|---|---|---|---|---|---|
| 7 | C(O) | Cl | Br | H | —CH$_2$COOH | —CH$_2$-pyridin-3-yl | 0 |
| 8 | C(O) | Cl | Br | H | —COOH | phenyl | 1 |
| 9 | C(O) | Cl | Cl | H | —COOH | phenyl | 0 |
| 10 | C(O) | Cl | Cl | H | —COOH | benzyl | 0 |
| 11 | C(O) | Cl | Cl | H | —CH$_2$COOH | phenyl | 0 |
| 12 | C(O) | Cl | Cl | H | —COOH | —CH$_2$-benzyl | 0 |
| 13 | C(O) | Cl | Cl | H | —COOH | phenyl | 0 |
| 14 | C(O) | Cl | Cl | H | —COOH | benzyl | 0 |
| 15 | C(O) | Cl | Cl | H | —CH$_2$COOH | —CH$_2$-benzyl | 0 |
| 16 | C(O) | Cl | Br | H | —CH$_2$COOH | —CH$_2$-benzyl | 0 |
| 17 | C(O) | Cl | Cl | H | —CH$_2$COOH | 4-methoxybenzyl | 0 |
| 18 | C(O) | Cl | Cl | H | —COOH | 4,5-dimethoxy-phenyl | 1 |
| 19 | C(O) | Cl | Cl | H | —CH$_2$COOH | 2-chlorobenzyl | 0 |
| 20 | C(O) | Cl | Cl | H | —COOH | phenyl | 1 |
| 21 | C(0) | Cl | Br | H | —CH$_2$COOH | 3-methoxybenzyl | 0 |
| 22 | C(O) | Cl | Cl | H | —COOH | 2-chlorobenzyl | 0 |
| 23 | C(O) | Cl | Cl | H | —COOH | —CH$_2$-pyridin—2-yl | 0 |
| 24 | C(O) | Cl | Cl | H | —COOH | —CH$_2$-benzyl | 0 |
| 25 | C(O) | Cl | Cl | H | —CH$_2$COOH | benzyl | 0 |
| 26 | C(O) | Cl | Cl | H | —CH$_2$COOH | phenyl | 0 |
| 27 | C(O) | Cl | Cl | H | —COOH | —CH$_2$-pyridin-3-yl | 0 |
| 28 | C(O) | Cl | Cl | H | —CH$_2$COOH | 2-methoxybenzyl | 0 |
| 29 | C(O) | Cl | Cl | H | —CH$_2$COOH | —CH$_2$-pyrimidin-3-yl | 0 |
| 30 | C(O) | Cl | Cl | H | —CH$_2$COOH | 3-methoxybenzyl | 0 |
| 31 | C(O) | Cl | Cl | H | —CH$_2$COOH | benzyl | 0 |
| 32 | C(O) | CH$_3$ | Br | H | —CH$_2$COOH | benzyl | 0 |

EXAMPLE 2

Preparation of 2,4-dichloro-N-[2-(indan-yloxy)-ethyl]-N-(1H-tetrazol-5-ylmethyl)benzenesulfonamide 3-Aminopropionitrile (0.190 g, 2.71 mmol, 1.2eq.) in anhydrous dimethylformamide (1 ml), benzoriazole (0.305g, 2.26 mmol, 1 eq), and 1,3-dicyclohexylcarbodiimide (0.466 g, 2.26 mmol, 1.0 eq) is added to a stirred solution of {(2,4-dichloro-benzenesulfonyl)-[2-(indan-5-yloxy)ethyl]-amino}-acetic acid (1.0 g, 2.26 mmol, 1.0 eq) in dimethylformamide (10 ml) at 0° under nitrogen, and the mixture allowed to warm to room temperature overnight. The reaction mixture is poured into saturated sodium bicarbonate solution (20 ml), extracted with NaCO$_3$ solution, and then extracted with EtOAc (3×20 ml). The combined organic extracts are washed with water (3×25 ml) and then with brine (25 ml), dried over MgSO$_4$, filtered, and concentrated to give the crude product (1.18 g). The crude product is triturated with Et$_2$O (2×50 ml), collected by filtration (0.826 g) and then purified by silica gel chromatography (eluent 5% MeOH—CH$_2$Cl$_2$), to give pure N-(2-cyano-ethyl)-2-{(2,4-dichlorobenzenesuphonyl)-[2-(indan-5-yloxy)-ethyl]-amino}-acetamide.

Triphenylphosphine (0.387 g, 1.47 mmol, 1.0 eq.), diethyl azodicarboxylate (0.256 g, 1.47 mmol, 1.0 eq.), and trimethylsilyl azide are added to a stirred solution of N-(2-cyano-ethyl)-2-{(2,4-dichlorobenzenesuphonyl)-[2-(indan-5-yloxy)-ethyl]-amino}-acetamide (0.732 g, 1.47 mmol, 1.0 eq.) in anhydrous THF (15 ml) at room temperature and allowed to stir overnight. Another 1 eq. of each Triphenylphosphine, diethylazodicarboxylate, trimethylsilyl azide is added to the reaction mixture, which is heated at 40° C. (oil-bath temperature) for 6 hours. The reaction mixture is cooled to 0° C. and excess ammonium cerium (IV) nitrate solution (5.5%, 120 ml, 12 mmol) is added slowly. The reaction mixture is concentrated and stirred in EtOAc (300 ml) at room temperature overnight. The solution is filtered, dried over MgSO$_4$, and concentrated to give a crude oil (2.25 g), which is purified by silica gel chromatography (eluent: EtOAc-Hexane (1:2 then 1:1 then 1:0), to afford pure 2,4-dichloro-N-[1-(2-cyano-ethyl)-1H-tetrazol-5-ylmethyl]-N-[2-(indan-5-yloxy)-ethyl]benzene sulfonamide.

1 M NaOH solution (0.63 mmol, 1.0 eq) is added to a stirred solution of 2,4-dichloro-N-[1-(2-cyano-ethyl)-1H-tetrazol-5-ylmethyl]-N-[2-(indan-5-yloxy)-ethyl]benzene sulfonamide (0.325 g, 1 eq.) in tetrahydrofuran (3 ml) at room temperature and the reaction mixture stirred overnight. The reaction mixture is acidified with 1 M HCl solution to pH 3, and then extracted with EtOAc (20 ml). The organic extract is washed with 1 M HCl solution (2×5 ml), and then with brine (1×10 ml), dried over MgSO$_4$, and concentrated to give a crude solid (0.211 g), which is triturated with Et$_2$O, filtered, washed with $Et_2O$ and dried under suction. The solid is purified by preparative HPLC to give pure 2,4-dichloro-N-[2-(indan-5-yloxy)-ethyl]-N-(1H-tetrazol-5-yl-methyl)benzene-sulfonamide.

In the following examples compounds of formula I wherein $R^1$ is indan-5-yl, and m is 2 are prepared analogously to example 2 or process c (see page 3).

| Example | $R^2$ | $R^3$ | $R^4$ | $R^5$ | $R^6$ |
|---------|-------|-------|-------|-------|-------|
| 33 | Cl | Cl | H | H | tetrazol-5-yl |
| 34 | Cl | Cl | H | H | $CH_2OH$ |
| 35 | Cl | Cl | H | H | $CH_2NHCH(CH_2COOH)$benzyl |

Characterising Data

Compounds of the above tables are found to exhibit the following HPLC retention data [min] and/or ion mass:

| Ex. | RT [min] | Ion mass |
|-----|----------|----------|
| 2  | 7.0 | $MH^+$ = 443 |
| 3  | 7.1 | $MH^+$ = 444 |
| 4  | 6.6 | $MH^+$ = 529 |
| 5  | 7.6 | $MH^+$ = 488 |
| 6  | 7.2 | $MH^+$ = 529 |
| 7  | 5.5 | $MH^+$ = 650 |
| 8  | 7.7 | $MH^+$ = 635 |
| 9  | 8.0 | $MH^+$ = 577 |
| 10 | 8.1 | $MH^+$ = 591 |
| 11 | 7.7 | $MH^+$ = 591 |
| 12 | 8.2 | $MH^+$ = 605 |
| 13 | 8.0 | $MH^+$ = 577 |
| 14 | 8.1 | $MH^+$ = 591 |
| 15 | 8.2 | $MH^+$ = 619/621 |
| 16 | 8.7 | $MH^+$ = 663 |
| 17 | 7.8 | $MH^+$ = 635 |
| 18 | 7.3 | $MH^+$ = 651 |
| 19 | 8.1 | $MH^+$ = 639 |
| 20 | 7.7 | $MH^+$ = 591 |
| 21 | 9.2 | $MH^+$ = 679 |
| 22 | 8.2 | $MH^+$ = 625 |
| 23 | 5.7 | $MH^+$ = 592 |
| 24 | 8.2 | $MH^+$ = 605 |
| 25 | 8.0 | $MH^+$ = 605 |
| 26 | 7.8 | $MH^+$ = 591 |
| 27 | 5.5 | $MH^+$ = 592 |
| 28 | 8.0 | $MH^+$ = 635 |
| 29 | 5.5 | $MH^+$ = 606 |
| 30 | 7.9 | $MH^+$ = 635 |
| 31 | 8.1 | $MH^+$ = 605 |
| 32 | 7.9 | $MH^+$ = 629 |
| 33 | 7.3 | $MH^+$ = 468 |
| 34 | 7.5 | $MH^+$ = 4+ |
| 35 | 6.5 | $MH^+$ = 591 |

HPLC conditions: Kingsorb 3 micron, +x 4.6 mm C 18 column, Gradient elution 10 to 100% acetonitrile in water (+0.1% trifluoroacetic acid) over 10 min.

The preferred compound of formula I for use in accordance with the invention are compounds of Example 5. These compounds are potent bradykinin antagonists, in vitro with a $K_I$ value of about 0.3 μM.

The invention claimed is:

1. A compound of formula I (I)

$R^1$ is phenyl, 1,2-dichlorophenyl, 3-methylphenyl, 3-bromophenyl, naphth-2-yl, indan-5-yl benzo[1,3]dioxol-5-yl or 1,2,3,4-tetrahydronaphth-6-yl;

$R^2$ is hydrogen, halogen, unsubstituted $C_1$–$C_4$alkyl or substituted $C_0$–$C_4$alkyl;

$R^3$ is hydrogen, halogen or $C_1$–$C_4$alkyl;

$R^4$ is hydrogen or $C_1$–$C_4$alkyl;

$R^5$ is hydrogen or $C_1$–$C_4$alkyl;

$R^6$ is $CH_2OH$; tetrazol-5-yl; 1,2,4-triazol-5-yl; 1,2,3-triazol-5-yl; C(O)OH, C(O)$NH_2$; or $ZNH(CH_2)_nCHR^7R^8$, wherein Z is —C(O)— or —$CH_2$—, n is zero, 1, 2, 3 or 4;

$R^7$ is unsubstituted or substituted $C_1$–$C_4$alkyl, C(O)OH, C(O)O$C_1$–$C_4$alkyl;

$R^8$ is hydrogen, unsubstituted or substituted $C_1$–$C_4$alkyl, unsubstituted or substituted $C_5$–$C_{10}$aryl or hetero$C_5$–$C_{10}$aryl or $C_1$–$C_4$alkyl$C_5$–$C_{10}$aryl or $C_1$–$C_4$alkyl-hetero$C_5$–$C_{10}$aryl, hetero$C_5$–$C_{10}$aryl comprising one or more heteroatoms selected from N, O, and S; and m is 2, 3 or 4, in free form or in form of a salt.

2. The compound of claim 1, wherein $R^1$ is indan-5-yl, $R^2$ is Cl, $R^3$ is Br, $R^4$ is H, $R^5$ is H, and $R^6$ is C(O)OH, in free acid form or in form of a salt.

3. A process for the production of a compound of formula I as defined in claim 1, comprising
  a) for the production of a compound of formula I wherein $R^6$ is C(O)OH, deprotecting a compound of formula II (II)

wherein $R^1$, $R^2$, $R^3$, $R^4$, $R^5$ and m are as defined in claim 1 and $R^9$ is $C_1$–$C_4$alkyl; or (b) for the production of a compound of formula I wherein, $R^6$ is C(O)$NH_2$ or $ZNH(CH_2)_nCHR^7R^8$ wherein Z is —C(O)— and n, $R^7$ and $R^8$ are as defined in claim 1, reacting a compound of formula I wherein $R^6$ Is C(O)OH with $NH_3$ or a compound of formula III $HNH(CH_2)_nCHR^7R^8$ (III)

wherein n, $R^7$, and $R^8$ are as defined in claim 1;
and optionally further derivatising the resulting compound; or (c) for the production of a compound of formula I wherein, Ra is $CH_2OH$; tetrazol-5-yl; 1,2,4-triazol-5-yl and 1,2,3-triazol-5-yl or ZNH(CH$_2$)$_n$CHR$^7$R$^8$ wherein Z is —CH$_2$— and n, R$^7$ and R$^8$ are as defined in claim 1, reacting a compound of formula IV

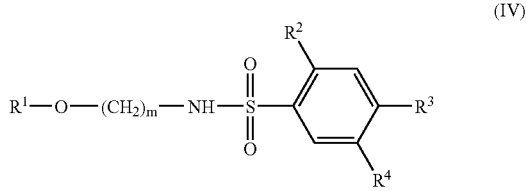

(IV)

wherein R$^1$, R$^2$, R$^3$, R$^4$ and m are as defined in claim 1, with a compound of formula V

(V)

wherein R$^5$ is as defined in claim 1, R$^6$ is CH$_2$OH, tetrazol-5-yl; 1,2,4-triazol-5-yl and 1,2,3-triazol-5-yl or ZNH(CH$_2$)$_n$CHR$^7$R$^8$ wherein Z is —CH$_2$— and n, R$^8$ and R$^9$ are as defined in claim 1 and Hal is halogen; and recovering the so obtained compound of formula I in free form or in form of a salt.

4. A compound of formula I as defined in claim 1 in free form or in form of a pharmaceutically acceptable salt, for use as a pharmaceutical.

5. A pharmaceutical composition comprising a compound of formula I as defined in claim 1 in free form or in form of a pharmaceutically acceptable salt and a carrier.

6. A method for treating a disease or condition in which bradykinin B$_1$ receptor activation plays a role or is implicated wherein said disease or condition is selected from the group consisting of pain, inflammation, oedema, Crohn's disease, ulcerative colitis, pancreatitis and multiple sclerosis comprising administering to a mammal in need thereof a therapeutically effective amount of a compound of formula I as defined in claim 1 in free form or in form of a pharmaceutically acceptable salt and a carrier.

7. A compound of formula II

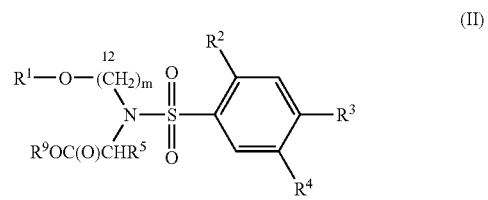

(II)

wherein R1, R$^2$, R$^3$, R$^4$, R$^5$ and m are as defined in claim 1 and R$^9$ is C$_1$–C$_4$alkyl, in free form or in form of a salt.

8. A combination comprising a therapeutically effective amount of a compound of formula I as defined in claim 1 in free form or in form of a pharmaceutically acceptable salt and a second drug substance, said second drug substance being for example for use in the treatment of pain, inflammation, oedema, Crohn's disease, ulcerative colitis, pancreatitis or multiple sclerosis.

* * * * *